United States Patent
Kim et al.

(10) Patent No.: US 10,589,095 B2
(45) Date of Patent: Mar. 17, 2020

(54) DEVICE FOR TREATING DISORDERS OF SECRETING GLAND IN EYELID

(71) Applicants: ILOODA Co., Ltd., Suwon-si, Gyeonggi-do (KR); Lid Lab Corp., Hanam-si, Gyeonggi-do (KR)

(72) Inventors: Young Han Kim, Suwon-si (KR); Dong Hun Moon, Suwon-si (KR); Myoung Joon Kim, Seoul (KR)

(73) Assignees: ILOODA Co., Ltd., Suwon-si, Gyeonggi-do (KR); Lid Lap Corp., Hanam-si, Gyeonngi-do (KR)

( * ) Notice: Subject to any disclaimer, the term of this patent is extended or adjusted under 35 U.S.C. 154(b) by 107 days.

(21) Appl. No.: 15/952,199

(22) Filed: Apr. 12, 2018

(65) Prior Publication Data

US 2018/0304079 A1    Oct. 25, 2018

(30) Foreign Application Priority Data

Apr. 24, 2017  (KR) .......................... 10-2017-0052184

(51) Int. Cl.
*A61N 1/36* (2006.01)
*A61N 1/05* (2006.01)
*A61F 9/007* (2006.01)

(52) U.S. Cl.
CPC .......... *A61N 1/36046* (2013.01); *A61F 9/007* (2013.01); *A61F 9/00772* (2013.01); *A61N 1/3606* (2013.01); *A61N 1/0526* (2013.01); *A61N 1/36014* (2013.01)

(58) Field of Classification Search
CPC .............. A61N 1/36046; A61N 1/3606; A61N 1/36014
See application file for complete search history.

(56) References Cited

U.S. PATENT DOCUMENTS

2013/0053733 A1* 2/2013 Korb ...................... A61N 1/403
                                                        601/2

FOREIGN PATENT DOCUMENTS

| KR | 10-2014-0054002 A | 5/2014 |
| KR | 10-2015-0054996 A | 5/2015 |
| KR | 10-2016-0104747 A | 9/2016 |

* cited by examiner

*Primary Examiner* — Paula J Stice
(74) *Attorney, Agent, or Firm* — Revolution IP, PLLC

(57) ABSTRACT

Disclosed is a device for treating disorders of a secreting gland in an eyelid. The device includes an eyeball protection cap for covering an eyeball of a patient to protect the eyeball, and a support body for fixing the eyeball protection cap and enabling an eyelid of the patient to be located between the eyeball protection cap and the support body in order to support the eyelid in the state of being in contact with the eyelid, wherein the eyeball protection cap is configured such that the inner surface of the eyeball protection cap covers the eyeball in order to protect the eyeball and the outer surface of the eyeball protection cap contacts the inner surface of the eyelid, which is located between the eyeball protection cap and the support body, in order to provide electrical stimulation to a secreting gland in the eyelid such that a secretion is smoothly secreted from the secreting gland.

2 Claims, 5 Drawing Sheets

DEVICE FOR TREATING DISORDERS OF SECRETING GLAND IN EYELID

BACKGROUND OF THE INVENTION

Field of the Invention

The present invention relates to a device for treating disorders of a secreting gland in an eyelid, and more particularly to a device for treating disorders of a secreting gland in an eyelid that is capable of directly providing stimulation to an eyelid of a patient in order to treat diseases that may be caused by disorders of a secreting gland in the eyelid, such as dry-eye syndrome.

Description of the Related Art

A dry-eye syndrome, which is also called a dysfunctional tear syndrome, is a disease that is caused as the result of a reduction or change in the amount and quality of a tear layer, which functions to gently wet an eye such that the eye is maintained in a soft and comfortable state.

FIG. 1 is a side sectional view showing a general eye. An eye lens 11 is located in front of an eyeball 10, and a cornea 12 is located in front of the eye lens 11. Tears are secreted from a lachrymal gland located in an upper eyelid 20, which covers the cornea 12 in order to maintain the eye in gentle conditions.

A fat secretion gland, namely a Meibomian gland 22, is located in a lower eyelid 20 as well as in the upper eyelid 20. Fat secreted from the Meibomian gland 22 forms the uppermost layer of a tear film. The fat layer, which is formed at the uppermost layer of the tear film, prevents the evaporation of tears such that the eye is maintained in gentle conditions.

In the case in which the Meibomian gland 22 in the eyelid 20 malfunctions, whereby fat is not appropriately secreted from the Meibomian gland 22, no fat layer is appropriately formed at the uppermost layer of the tear film. As a result, tears may easily evaporate, which frequently leads to a dry-eye syndrome.

In the case in which the Meibomian gland 22 malfunctions, a discharge pipe of the Meibomian gland 22 may be clogged, which may cause chalazion, in which a fat secretion gathers in the hypoderm of the eyelid, in addition to the occurrence of a dry-eye syndrome.

There are a large number of prior art documents related to compositions for treating diseases that are caused due to disorders of the Meibomian gland, such as a dry-eye syndrome, through the injection of medicinal substances.

For example, some of the prior art documents include Korean Patent Application No. 10-2015-7009315, Korean Patent Application No. 10-2016-0104747, and Korean Patent Application No. 10-2014-7002457.

In the case in which medicinal substances are injected into the eye in order to treat secretion-related disorders of the Meibomian gland, as described above, however, portions other than the portion that needs to be treated are affected by the medicinal substances, since antibiotics for inflammation treatment are contained in the medicinal substances. Therefore, there is an urgent necessity to develop a method of providing physical stimulation to the eyelid in order to treat secretion-related disorders of the Meibomian gland.

SUMMARY OF THE INVENTION

Therefore, the present invention has been made in view of the above problems, and it is an object of the present invention to provide a device for treating disorders of a secreting gland in an eyelid that is mounted on an eye of a patient in order to treat the eye using a mechanical method, wherein the device is capable of directly applying electrical stimulation to an eyelid of the patient such that a secreting gland in the eyelid can function normally.

In accordance with an aspect of the present invention, the above and other objects can be accomplished by the provision of a device for treating disorders of a secreting gland in an eyelid, including an eyeball protection cap for covering an eyeball of a patient to protect the eyeball, and a support body for fixing the eyeball protection cap and enabling an eyelid of the patient to be located between the eyeball protection cap and the support body in order to support the eyelid in the state of being in contact with the eyelid, wherein the eyeball protection cap is configured such that the inner surface of the eyeball protection cap covers the eyeball in order to protect the eyeball and the outer surface of the eyeball protection cap contacts the inner surface of the eyelid, which is located between the eyeball protection cap and the support body, in order to provide electrical stimulation to a secreting gland in the eyelid such that a secretion is smoothly secreted from the secreting gland in the eyelid.

The eyeball protection cap may include an inner surface contact electrode unit connected to a signal generator for generating an electrical signal for providing electrical stimulation to the eyelid, the inner surface contact electrode unit including a plurality of electrodes provided on the outer surface of the eyeball protection cap in an exposed state and in the state of being in contact with the inner surface of the eyelid in order to provide the electrical stimulation transmitted from the signal generator to the secreting gland in the eyelid.

The eyeball protection cap may include an eyeball cover unit for covering the eyeball of the patient to protect the eyeball, a connection unit connected to the eyeball cover unit and supported by the support body in the state of being received in the support body, an inner surface contact electrode unit connected to a signal generator for generating an electrical signal for providing electrical stimulation to the eyelid, the inner surface contact electrode unit being provided on the outer surface of the eyeball protection cap in an exposed state and in the state of being in contact with the inner surface of the eyelid in order to provide the electrical stimulation transmitted from the signal generator to the secreting gland in the eyelid, and an insulation protecting unit provided on the inner surface of the eyeball cover unit in an insulated state in order to protect the eyeball from the electrical stimulation provided by the inner surface contact electrode unit.

The support body may include a main body unit provided so as to cover the outer surface of the eyelid, the main body unit being configured to receive one side of the eyeball protection cap in order to support the eyeball protection cap, and a contact support unit provided on the inner surface of the main body unit so as to contact the outer surface of the eyelid such that the outer surface of the eyeball protection cap is supported in the state of being in contact with the inner surface of the eyelid.

The support body may further include an outer surface contact electrode unit connected to a signal generator for generating an electrical signal for providing electrical stimulation to the eyelid, the outer surface contact electrode unit including a plurality of electrodes provided on the surface of the contact support unit that contacts the eyelid in an exposed state and in the state of being in contact with the outer surface of the eyelid in order to provide the electrical stimulation transmitted from the signal generator to the secreting gland in the eyelid.

In accordance with another aspect of the present invention, there is provided a device for treating disorders of a secreting gland in an eyelid, including an eyeball protection cap for covering an eyeball of a patient to protect the eyeball, and a support body for fixing the eyeball protection cap and enabling an eyelid of the patient to be located between the eyeball protection cap and the support body in order to support the eyelid in the state of being in contact with the eyelid, wherein the support body includes a contact support unit for contacting the outer surface of the eyelid such that the outer surface of the eyeball protection cap is supported in the state of being in contact with the inner surface of the eyelid, wherein the device further includes a first electrode unit connected to a signal generator for generating an electrical signal for providing electrical stimulation to the eyelid, the first electrode unit including a plurality of positive (+) electrodes or a plurality of negative (−) electrodes provided on the outer surface of the eyeball protection cap in an exposed state and in the state of being in contact with the inner surface of the eyelid, and a second electrode unit connected to the signal generator, the second electrode unit including a plurality of electrodes provided on the surface of the contact support unit that contacts the eyelid in an exposed state and in the state of being in contact with the outer surface of the eyelid, the electrodes of the first electrode unit and the electrodes of the second electrode unit having different polarities and each of the electrodes of the first electrode unit and a corresponding one of the electrodes of the second electrode unit electrically forming a pair, and wherein an electric field is generated by the respective pairs of electrodes between the first electrode unit, which contacts the inner surface of the eyelid, and the second electrode unit, which contacts the outer surface of the eyelid, according to the electrical signal generated by the signal generator, whereby the electrical stimulation is provided to a secreting gland in the eyelid.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Hereinafter, a device for treating disorders of a secreting gland in an eyelid according to the present invention will be described in detail with reference to the accompanying drawings.

First, the construction and operation of a device for treating disorders of a secreting gland in an eyelid according to an embodiment of the present invention will be described with reference to FIGS. 2 and 3.

Figure 1:
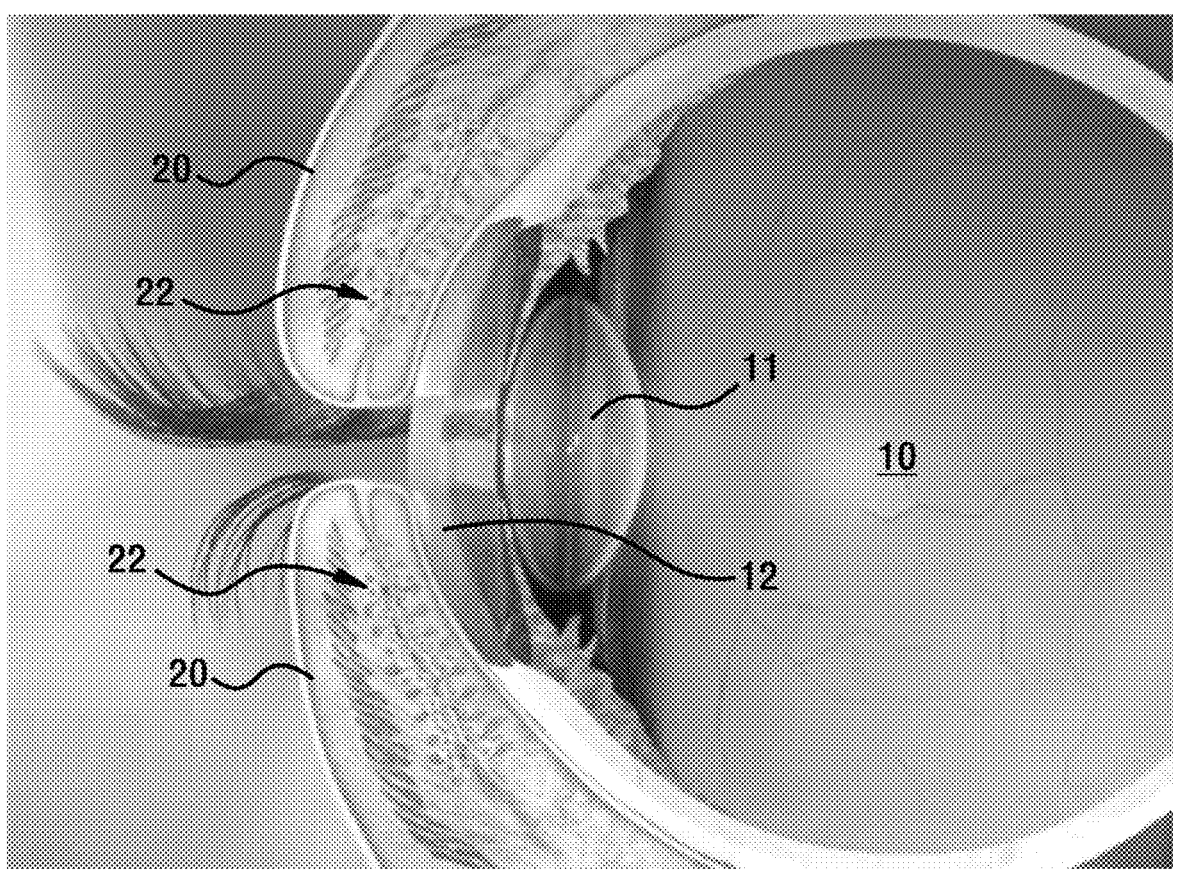
FIG. 1 is a side sectional view showing a general eye.
Figure 2:
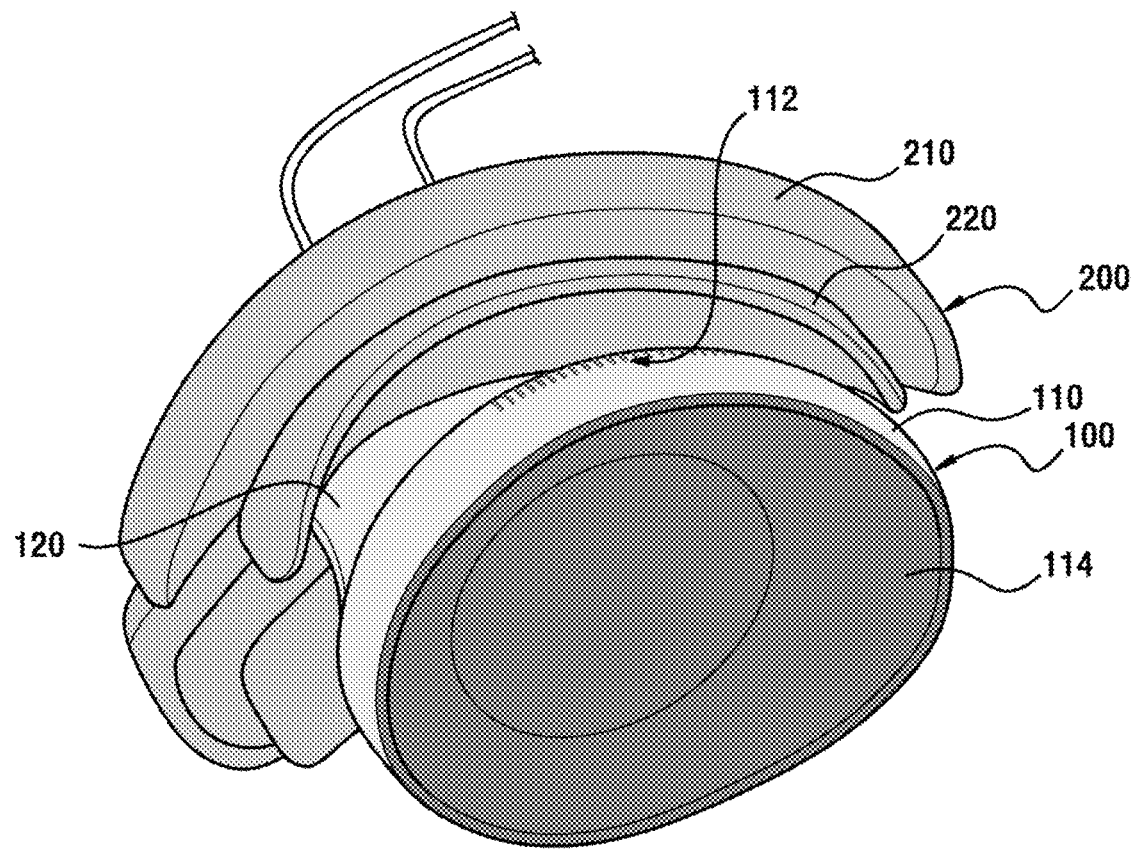
FIG. 2 is a view showing the construction of a device for treating disorders of a secreting gland in an eyelid according to an embodiment of the present invention.
Figure 3:
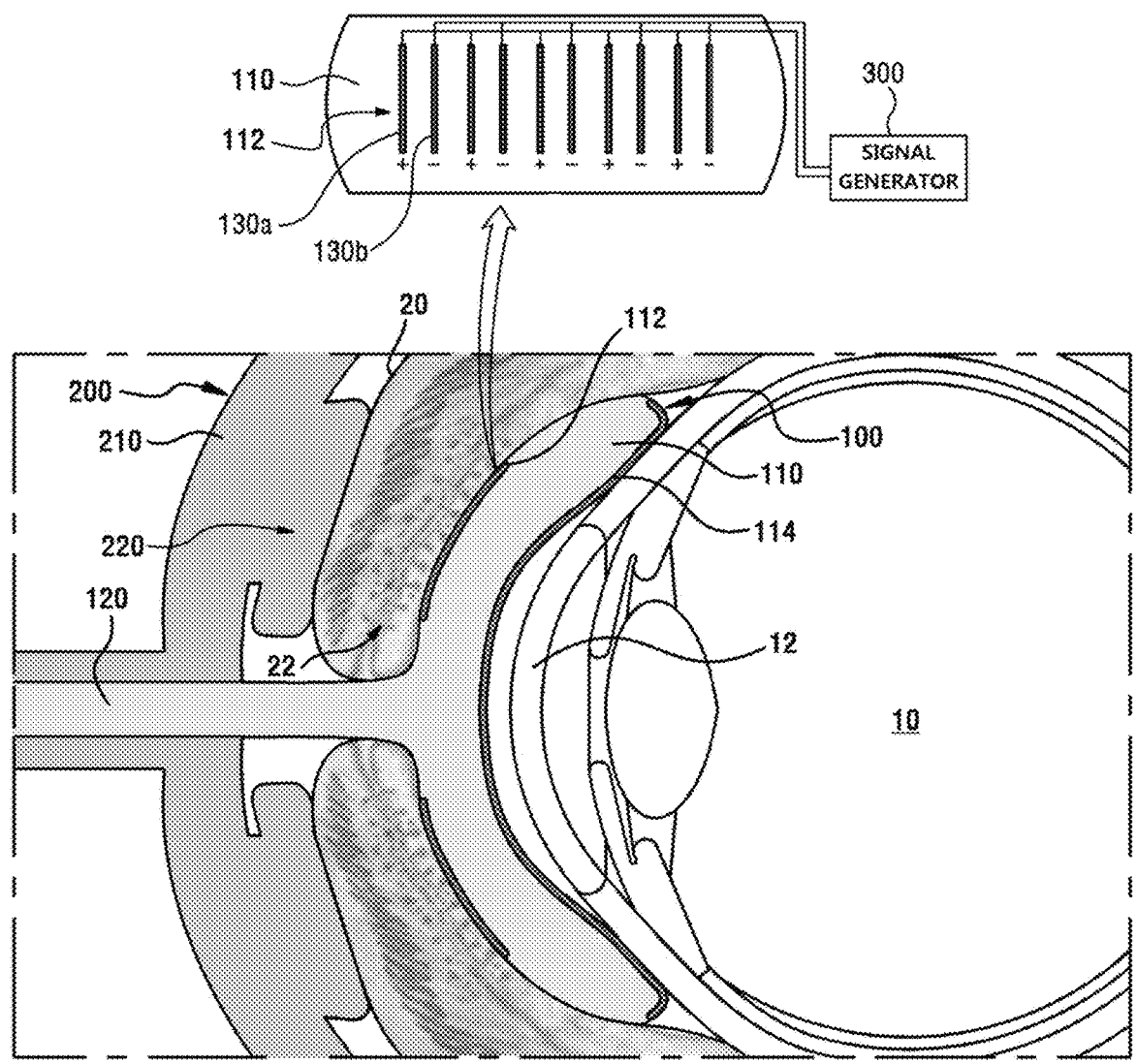
FIG. 3 is a side sectional view showing the state in which the treatment device shown in FIG. 2 is mounted to an eyeball of a patient in order to provide electrical stimulation to an eyelid of the patient.

FIG. 2 is a view showing the construction of a device for treating disorders of a secreting gland in an eyelid according to an embodiment of the present invention, and FIG. 3 is a side sectional view showing the state in which the treatment device shown in FIG. 2 is mounted to an eyeball of a patient in order to provide electrical stimulation to an eyelid of the patient.

A treatment device according to an embodiment of the present invention shown in FIGS. 2 and 3 is configured to be mounted to an eye of a patient. Basically, the treatment device may include an eyeball protection cap 100 for covering an eyeball 10 of a patient to protect the eyeball 10 and a support body 200 for fixing the eyeball protection cap 100 and enabling an eyelid 20 to be located between the eyeball protection cap 100 and the support body 200 in order to support the eyelid 20 in the state of being in contact with the eyelid 20.

The eyeball protection cap 100 includes an eyeball cover unit 110, the inner surface of which is concavely formed in order to cover the eyeball 10 of the patient such that the eyeball 10 can be protected and the outer surface of which is formed so as to contact the inner surface of the eyelid 20 of the patient, and a connection unit 120 extending from the outer surface of the eyeball cover unit 110 toward the opposite side of the concavely formed inner surface of the eyeball cover unit 110 so as to be received in the support body 200.

On the outer surface of the eyeball cover unit 110 is provided an inner surface contact electrode unit 112 including a plurality of electrodes 130a and 130b, which are configured to contact the inner surface of the eyelid 20 of the patient in order to transmit electrical stimulation to the eyelid 20 such that the electrical stimulation is provided to a secreting gland, such as a Meibomian gland 22, in the eyelid 20.

As shown in FIGS. 2 and 3, the inner surface contact electrode unit 112 is configured such that a plurality of positive (+) electrodes 130a and a plurality of negative (−) electrodes 130b are provided on the outer surface of the eyeball cover unit 110 in pairs in an exposed state. The inner surface contact electrode unit 112 is connected to a signal generator 300, which is provided at the outside, such that an electrical signal generated by the signal generator 300 is transmitted to the eyelid 20 of the patient via the inner surface contact electrode unit 112. When the electrical signal generated by the signal generator 300 is applied to the positive (+) electrodes 130a and the negative (−) electrodes 130b of the inner surface contact electrode unit 112, an electric field is generated between each pair of positive (+) and negative (−) electrodes 130a and 130b, whereby electrical stimulation is provided to the eyelid 20 of the patient. Alternatively, the inner surface contact electrode unit 112 may be configured such that active electrodes are provided instead of the positive (+) and negative (−) electrodes and a ground electrode is connected to each of the active electrodes, whereby the active electrodes can provide electrical stimulation to the eyelid 20 of the patient according to the electrical signal generated by the signal generator 300.

The frequency and magnitude ranges of the electrical signal generated by the signal generator may be preset so as to apply appropriate stimulation while preventing damage to the thin and weak tissue of the eyelid of the patient such that the electrical signal can be generated within the preset frequency and magnitude ranges thereof.

For example, the signal generator 300 may generate a weak low-frequency signal, and the inner surface contact electrode unit 112 may apply low-frequency stimulation to the Meibomian gland 22 in the eyelid 20 of the patient in response to the signal generated by the signal generator 300 such that disorders of the Meibomian gland 22 can be treated by the stimulation.

Inner surface contact electrode units 112 may be provided for both an upper eyelid and a lower eyelid in order to apply stimulation to the upper eyelid and the lower eyelid. In FIG. 3, only the components of the treatment device according to the present invention provided for the upper eyelid are denoted by reference numerals. However, this is in order to prevent duplication, and therefore it should be understood that the components of the treatment device according to the present invention provided for the lower eyelid are denoted by the same reference numerals although not mentioned additionally.

On the inner surface of the eyeball cover unit 110, which contacts the eyeball 10 of the patient, may be provided an insulation protecting unit 114 for preventing electricity from the inner surface contact electrode unit 112 from being transmitted to the eyeball 10 in order to safely protect the eyeball 10.

Meanwhile, as shown in FIGS. 2 and 3, the support body 200 includes a main body unit 210 for covering the outer surface of the eyelid 20 of the patient and receiving the connection unit 120 of the eyeball protection cap 100 in order to support the connection unit 120, and a contact support unit 220 provided on the inner surface of the main body unit 210 so as to contact the outer surface of the eyelid 20 such that the outer surface of the eyeball cover unit 110 is supported in the state of being in contact with the inner surface of the eyelid 20.

That is, as shown in FIG. 3, the eyelid 20 is located between the contact support unit 220 and the eyeball cover unit 110, and the contact support unit 220 is in tight contact with the eyelid 20, whereby the outer surface of the eyeball cover unit 110 is supported in the state of being in contact with the inner surface of the eyelid 20.

In the embodiment shown in FIGS. 2 and 3, the inner surface contact electrode unit 112 is provided on the outer surface of the eyeball cover unit 110 such that the inner surface contact electrode unit 112 provides electric stimulation in the state of being in tight contact with the inner surface of the eyelid 20 of the patient by the contact support unit 220. However, the present invention is not limited thereto, and various other embodiments of the present invention may be provided.

Figure 4:
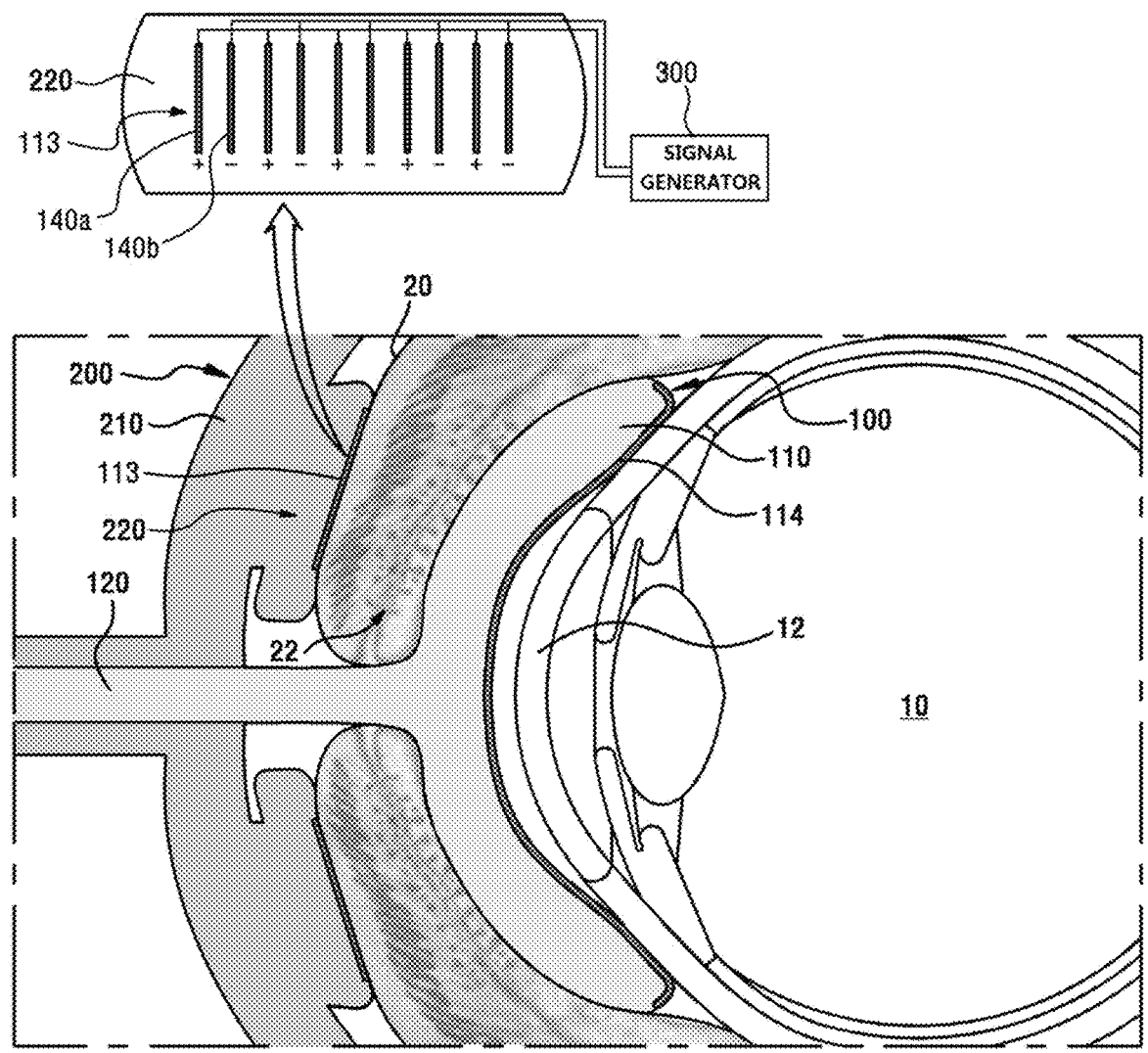
FIG. 4 is a side sectional view showing the state in which a device for treating disorders of a secreting gland in an eyelid according to another embodiment of the present invention is mounted to an eyeball of a patient in order to provide electrical stimulation to an eyelid of the patient.

In an example, as shown in FIG. 4, the contact support unit 220 may have a contact surface for contacting the eyelid 20 of the patient such that an electrode unit for providing electrical stimulation to the eyelid 20 contacts the outer surface of the eyelid 20 in order to provide electrical stimulation to the eyelid 20. Hereinafter, an electrode unit including a plurality of electrodes provided on the contact surface of the contact support unit 220, which contacts the eyelid 20, will be referred to as an outer surface contact electrode unit 113.

As shown in FIG. 4, the outer surface contact electrode unit 113 may also be connected to a signal generator 300 for generating an electrical signal for electrical stimulation, and may include a plurality of pairs of positive (+) and negative (−) electrodes 140*a* and 140*b*.

When the electrical signal generated by the signal generator 300 is applied to the positive (+) electrodes 140*a* and the negative (−) electrodes 140*b* of the outer surface contact electrode unit 113, an electric field is generated between each pair of positive (+) and negative (−) electrodes 140*a* and 140*b*, whereby electrical stimulation is provided to the eyelid 20 of the patient. Alternatively, the inner surface contact electrode unit 112 may be configured such that active electrodes are provided instead of the positive (+) and negative (−) electrodes and a ground electrode is connected to each of the active electrodes, whereby the active electrodes can provide electrical stimulation to the eyelid 20 of the patient according to the electrical signal generated by the signal generator 300.

As described above, the device for treating disorders of the secreting gland in the eyelid according to the present invention may be operated in both a mode in which the inner surface contact electrode unit 112 provides electrical stimulation to the inner surface of the eyelid 20 of the patient, as shown in FIG. 3, and a mode in which the outer surface contact electrode unit 113 provides electrical stimulation to the outer surface of the eyelid 20 of the patient, as shown in FIG. 4. Furthermore, one of the two modes may be selectively executed depending on the state of the eyelid 20 of the patient.

That is, in the device for treating disorders of the secreting gland in the eyelid according to the present invention, the eyeball protection cap 100 may be coupled to the support body 200. The eyeball protection cap 100 may be configured so as to be provided with the inner surface contact electrode unit 112 (hereinafter, referred to as "A-1"). In addition, the eyeball protection cap 100 may be configured so as not to be provided with the inner surface contact electrode unit 112 (hereinafter, referred to as "A-2"). Meanwhile, the contact support unit 220 of the support body 200 may be configured so as to be provided with the outer surface contact electrode unit 113 (hereinafter, referred to as "B-1"). In addition, the contact support unit 220 of the support body 200 may be configured so as not to be provided with the outer surface contact electrode unit 113 (hereinafter, referred to as "B-2"). In the case in which it is necessary to provide electrical stimulation on the inner surface of the eyelid of the patient depending on the state of the eyelid, the eyeball protection cap A-1 and the support body B-2 may be selected and coupled to each other for use. In the case in which it is necessary to provide electrical stimulation on the outer surface of the eyelid of the patient depending on the state of the eyelid, the eyeball protection cap A-2 and the support body B-1 may be selected and coupled to each other for use. Consequently, medical treatment suitable for the patient may be selectively performed.

Figure 5:
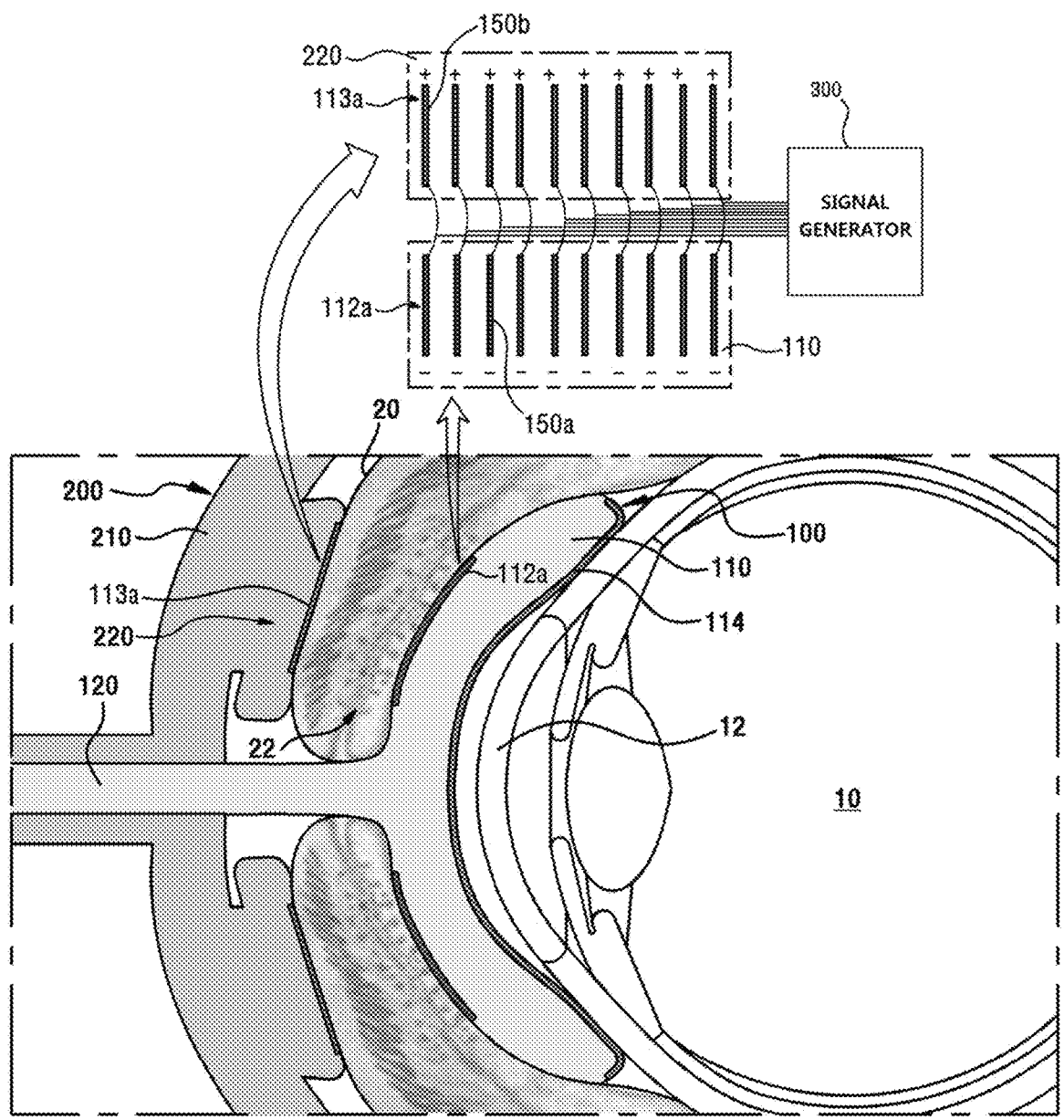
FIG. 5 is a side sectional view showing the state in which a device for treating disorders of a secreting gland in an eyelid according to a further embodiment of the present invention is mounted to an eyeball of a patient in order to provide electrical stimulation to an eyelid of the patient.

Meanwhile, a device for treating disorders of a secreting gland in an eyelid according to a further embodiment of the present invention shown in FIG. 5 is configured to have a structure in which electrodes having different polarities are provided on the inner surface and the outer surface of the eyelid 20 of the patient in the state in which the electrodes having different polarities are arranged in pairs such that each pair of electrodes provides electrical stimulation to the eyelid 20.

As shown in FIG. 5, the device for treating disorders of the secreting gland in the eyelid according to the embodiment of the present invention includes a first electrode unit 112a provided on the outer surface of the eyeball cover unit 110 in an exposed state, the first electrode unit 112a including a plurality of positive (+) electrodes or a plurality of negative (−) electrodes 150a configured to contact the inner surface of the eyelid 20 of the patient, and a second electrode unit 113a provided on the surface of the contact support unit 220 that contacts the eyelid 20 in an exposed state, the second electrode unit 113a including a plurality of negative (−) electrodes or a plurality of positive (+) electrodes 150b configured to contact the outer surface of the eyelid 20, wherein the electrodes 150a of the first electrode unit 112a and the electrodes 150b of the second electrode unit 113a have different polarities and wherein each of the electrodes 150a of the first electrode unit 112a and a corresponding one of the electrodes 150b of the second electrode unit 113a electrically form a pair.

The electrodes 150a of the first electrode unit 112a and the electrodes 150b of the second electrode unit 113a, which have different polarities, are connected to each other in pairs. The first electrode unit 112a and the electrodes of the second electrode unit 113a are connected to a signal generator 300 for generating an electrical signal for electrical stimulation. According to the electrical signal generated by the signal generator 300, an electric field is generated between the first electrode unit 112a, which contacts the inner surface of the eyelid 20 of the patient, and the second electrode unit 113a, which contacts the outer surface of the eyelid 20, whereby electrical stimulation is provided to the secreting gland in the eyelid 20.

For example, as shown in FIG. 5, the first electrode unit 112a may be configured such that a plurality of negative (−) electrodes 150a is arranged at predetermined intervals, and the second electrode unit 113a may be configured such that a plurality of electrodes 150b having polarity different from the polarity of the electrodes 150a of the first electrode unit 112a, i.e. a plurality of positive (+) electrodes, is arranged so as to correspond to the electrodes of the first electrode unit 112a in electrical pairs.

That is, each of the electrodes 150a of the first electrode unit 112a, i.e. the negative (−) electrode, and a corresponding one of the electrodes of the second electrode unit 113a, i.e. the positive (+) electrode 150b, may form a pair such that an electric field is generated between the two electrodes 150a and 150b by the signal generator 300, whereby electrical stimulation is provided to the eyelid 20 of the patient.

As described above, each of the electrodes of the first electrode unit 112a and a corresponding one of the electrodes of the second electrode unit 113a form a pair, and electrical stimulation is directly and effectively applied to the eyelid of the patient through each pair of electrodes such that the secreting gland in the eyelid can function normally.

As is apparent from the above description, the present invention provides a device for treating disorders of a secreting gland in an eyelid that is mounted on an eye of a patient in order to treat the eye using a mechanical method, wherein the device is capable of directly applying electrical stimulation to an eyelid of the patient such that a secreting gland in the eyelid can function normally.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for treating disorders of a secreting gland in an eyelid, comprising:
    an eyeball protection cap configured to cover an eyeball of a patient to protect the eyeball; and
    a support body configured to support the eyeball protection cap, wherein the support body comprises a contact support unit configured to contact and support the eyelid such that an outer surface of the eyeball protection cap is in contact with an inner surface of the eyelid and an inner surface of the contact support unit is in contact with an outer surface of the eyelid when the eyeball protection cap covers the eyeball of the patient,
    wherein the device further comprises:
    a first electrode unit connected to a signal generator for generating an electrical signal for providing electrical stimulation to the eyelid, the first electrode unit comprising a plurality of positive (+) electrodes or a plurality of negative (−) electrodes provided on the outer surface of the eyeball protection cap such that the first electrode unit is in contact with the inner surface of the eyelid; and
    a second electrode unit connected to the signal generator, the second electrode unit comprising a plurality of electrodes provided on the inner surface of the contact support unit such that the second electrode unit is in contact with the outer surface of the eyelid, the electrodes of the first electrode unit and the electrodes of the second electrode unit having different polarities and each of the electrodes of the first electrode unit and a corresponding one of the electrodes of the second electrode unit electrically forming a pair,
    wherein an electric field is generated by the respective pairs of electrodes between the first electrode unit and the second electrode unit according to the electrical signal generated by the signal generator, whereby the electrical stimulation is provided to a secreting gland in the eyelid.

2. The device according to claim 1, wherein the eyeball protection cap comprises:
    an eyeball cover unit configured to cover the eyeball of the patient to protect the eyeball, wherein the first electrode unit is provided on the outer of the eyeball cover unit;
    a connection unit connected to the eyeball cover unit and supported by the support body; and
    an insulation protecting unit provided on an inner surface of the eyeball cover unit in order to protect the eyeball from the electrical stimulation provided by the first electrode unit and the second electrode unit.

* * * * *